(12) United States Patent
Loken (10) Patent No.: US 7,045,295 B2
(45) Date of Patent: May 16, 2006

(54) METHOD FOR COLLECTING PURIFIED CELLS

(75) Inventor: Michael R Loken, Mercer Island, WA (US)

(73) Assignee: HematoLogics, Inc., Seattle, WA (US)

( * ) Notice: Subject to any disclaimer, the term of this patent is extended or adjusted under 35 U.S.C. 154(b) by 0 days.

(21) Appl. No.: 11/096,207

(22) Filed: Mar. 30, 2005

(65) Prior Publication Data

US 2005/0233362 A1    Oct. 20, 2005

Related U.S. Application Data

(60) Provisional application No. 60/558,977, filed on Apr. 2, 2004.

(51) Int. Cl.
*C12Q 1/68* (2006.01)
(52) U.S. Cl. .......................... 435/6; 435/91.2; 435/372; 536/23.1
(58) Field of Classification Search ..................... None
See application file for complete search history.

(56) References Cited

U.S. PATENT DOCUMENTS

| 5,496,562 | A | 3/1996 | Burgoyne | 424/488 |
| 5,756,126 | A | 5/1998 | Burgoyne | 424/488 |
| 5,807,527 | A | 9/1998 | Burgoyne | 424/488 |
| 6,124,012 | A | 9/2000 | Jones, Jr. et al. | 428/64.1 |
| 6,294,203 | B1 | 9/2001 | Burgoyne | 424/488 |
| 6,322,983 | B1 | 11/2001 | Burgoyne | 435/6 |
| 6,447,804 | B1 | 9/2002 | Burgoyne | 424/488 |
| 6,627,226 | B1 | 9/2003 | Burgoyne et al. | 424/488 |
| 6,645,717 | B1 | 11/2003 | Smith et al. | 435/6 |

OTHER PUBLICATIONS

FASCSVantage™SE, Flow Cytometry System, Becton Dickinson Product Brochure, Mar. 1998.
Parks, D.R. et al., "Fluorescence-Activated Cell Sorting: Theory, Experimental Optimization, and Applications in Lymphoid Cell Biology," *Methods in Enzymology 108*: 197-241, 1984.
Roederer, M. et al., "Flow Cytometry," in *Encyclopedia of Immunology*, 2$^{nd}$ Edition, P. Delves and I. Roitt (eds.), Academic Press Limited, London, 1998, pp. 933-943.
Stewart, C.C. et al. (eds.), *Immunophenotyping*, Wiley-Liss, New York, NY, 2000, pp. 153-160.

*Primary Examiner*—James Ketter
(74) *Attorney, Agent, or Firm*—Seed IP Law Group PLLC (57) ABSTRACT

The present invention provides improved methods for collecting cells for subsequent analysis. More specifically, the invention provides methods for collecting purified cell samples from a flow cytometer onto a solid support on which cell lysis occurs and genetic material is immobilized.

18 Claims, 4 Drawing Sheets

METHOD FOR COLLECTING PURIFIED CELLS

BACKGROUND OF THE INVENTION

1. Field of the Invention

The present invention relates generally to improved methods for collecting cells for subsequent analysis and more specifically, for collecting purified cells from a flow cytometer onto a solid support. Upon absorption onto the solid support, cell lysis occurs and genetic material from the lysed cells is immobilized on the solid support allowing analysis of the genetic material directly on the solid support or following an elution step.

2. Description of the Related Art

One method for isolating heterogeneous cell populations is by fluorescence activated cell sorting, originally developed by Herzenberg and co-workers (*Science*. 1969 166 (906):747–9; *J Histochem Cytochem*. 1976 24(1):284–91; *Clin Chem*. 1973 19(8):813–6; Ann. N.Y. Acad. of Sci. 1975 254:163–171). Using this technology, cells are labeled with antibodies conjugated to dyes. By combining multiple immunofluorescent labels with the light scattering properties of the cells it is possible to distinguish between cells of different lineages based on expression of unique cell surface antigens (See for example, Loken M R, et al., in *Flow Cytometry in Hematology*. Laerum O D, Bjerksnes R. eds. Academic Press. New York, pp 31–42, 1992; Civin C I, et al., in "*Concise Reviews in Clinical and Experimental Hematology*" Martin J. Murphy ed. AlphaMed Press, Dayton Ohio, 1992, pp 149–159). Populations identified by the flow cytometer can then be isolated using the cell sorting electronics available on the instrument. Two or more fractions can be obtained in pure or enriched forms for further analysis using molecular biology techniques.

One technical problem is the difficulty encountered in working with small numbers of purified cells or small sample volumes. It is well known in the field that a significant proportion of cells are lost in processing small numbers of cells, typically by adhesion to vessel walls, pipettes or other charged surfaces in which the cells come in contact.

Accordingly, there remains a need in the art for improved methods for collecting purified cells, particularly when handling small numbers of cells and/or small sample volumes. The present invention fulfills this need and other needs.

BRIEF SUMMARY OF THE INVENTION

As noted above, the present invention relates generally to improved methods for collecting cells for subsequent analysis and more specifically, for collecting purified cells from a flow cytometer onto a solid support. Upon absorption onto the solid support, cell lysis occurs and genetic material from the lysed cells is immobilized on the solid support allowing analysis of the genetic material directly on the solid support or following an elution step.

In one embodiment, the present invention provides a method for collecting purified cells for genetic analysis, comprising sorting a population of cells using a flow cytometer and collecting a purified cell in a drop of collection fluid; depositing the drop of collection fluid onto a solid support at a discrete location, the solid support comprising a cell lysing agent and a genetic material preservative; wherein the purified cell within the drop of collection fluid is absorbed by the solid support and lysed by the lysing agent to yield genetic material; and wherein the genetic material is sorbed by the solid support and protected from degradation by the genetic material preservative.

In one embodiment, the solid support is comprised of a cellulose-based substance. In certain embodiments the cellulose-based substances is cellulose, nitrocellulose or carboxymethylcellulose. In another embodiment, the solid support is comprised of hydrophilic polymers. In certain embodiments, the hydrophilic polymer is a polyester, a polyamide, or a carbohydrate polymer. In yet another embodiment, the solid support is comprised of glass, silica or quartz fibers.

In an additional embodiment, the discrete location is identifiable by a color indicator. In yet a further embodiment, two or more drops of collection fluid are deposited onto the same solid support. In certain embodiments, the two or more drops of collection fluid are deposited at the same discrete location.

In another embodiment, the present invention provides a method wherein at least a first and a second population of cells are sorted and wherein a drop of collection fluid containing a cell from the first population and a drop of collection fluid containing a cell from the second population are deposited each onto a separate solid support. In certain embodiments, the drop of collection fluid containing a cell from the first population and the drop of collection fluid containing a cell from the second population are deposited each at a distinct location onto the same solid support. In other embodiments, the drops containing cells from the different populations are deposited onto separate solid supports. Many distinct populations of cells can be sorted, as defined by immunofluorescent markers as described further herein. Accordingly, the present method provides for methods wherein at least one, two, three, four, five, six, or more distinct populations (fractions) of cells can be sorted and collected as described herein.

In a further embodiment, the genetic material sorbed onto the solid support by heat elution.

In another embodiment, the present invention provides a method wherein the genetic material is further analyzed using a polymerase chain reaction or short tandem repeats.

These and other aspects of the present invention will become apparent upon reference to the following detailed description and attached drawings.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. Further, all numerical ranges recited herein explicitly include all integer values within the range.

DETAILED DESCRIPTION OF THE INVENTION

The present invention relates generally to improved methods for collecting cells for subsequent analysis, in particular molecular genetic analysis. More specifically, the invention provides methods for collecting purified cell samples from a flow cytometer onto a solid support, such as a dry solid matrix, on which cell lysis occurs. Genetic material (GM) from the lysed cells is then immobilized on the matrix of the solid support. Analysis of the GM can be performed directly or can be done following an elution step. The GM is also extremely stable on the solid support and can be archived for later analysis.

Fluorescence Activated Cell Sorting

The technique of immunofluorescent staining is well known and can be carried out according to any of a variety of protocols, such as those described in Current Protocols in Cytometry (John Wiley & Sons, NY, N.Y., Eds. J. Paul Robinson, et al.). Generally, a biological sample, such as peripheral blood, bone marrow, lymph node tissue, cord blood, thymus tissue, tissue from a site of infection, spleen tissue, tumor tissue, and the like, is collected from a subject and cells are isolated therefrom using techniques known in the art. In one embodiment, blood is collected from a subject and any mature erythrocytes are lysed using a buffer, such as buffered $NH_4Cl$. The remaining leukocytes are washed and then incubated with antibodies (e.g., monoclonal antibodies) conjugated to any of a variety of dyes (fluorophores) known in the art (see for example, Glen Spectra, Middlesex, UK; URL address: glenspectra dot co dot uk slash glen slash filters slash fffluorpn dot htm or the following URL address: cellscience dot bio-rad dot com slash fluorescence slash fluorophoradata dot htm). Representative dyes in this context include, but are not limited to, FITC (Fluorescein Isothiocyante), R-phycoerytbrin (PE), Allophycocyanin (APC), Cy7®, and Texas Red.

A wide variety of antibodies known in the art, and specific antibodies generated using techniques well known in the art, are useful in the context of the present invention. Generally, the antibodies for use in the methods described herein are specific for a cell marker of interest, such as any of the CD cell surface markers (see for example the CD index at the National Center for Biotechnology Information (NCBI) web site at ncbi dot nlm dot nih dot gov slash PROW slash guide slash 45277084 dot html; or Current Protocols in Immunology, John Wiley & Sons, NY, N.Y.), cytokines, adhesion proteins, developmental cell surface markers, tumor antigens, or other proteins expressed by a cell population of interest. An antibody specific for virtually any protein expressed by a cell is useful in the context of this invention. Illustrative antibodies include antibodies that recognize, CD3, CD33, CD34, CD8, CD4, CD56, CD19, CD14, CD15, CD16, CD13, CD38, CD45, CD20, CD5, CD2, CD10.

After a period of incubation with a dye-conjugated antibody, typically about 20 minutes in the dark (incubation times may vary according to particular protocols), the leukocytes are washed with buffered saline and resuspended in buffered saline containing protein for introduction into a flow cytometer.

Figure 1A:
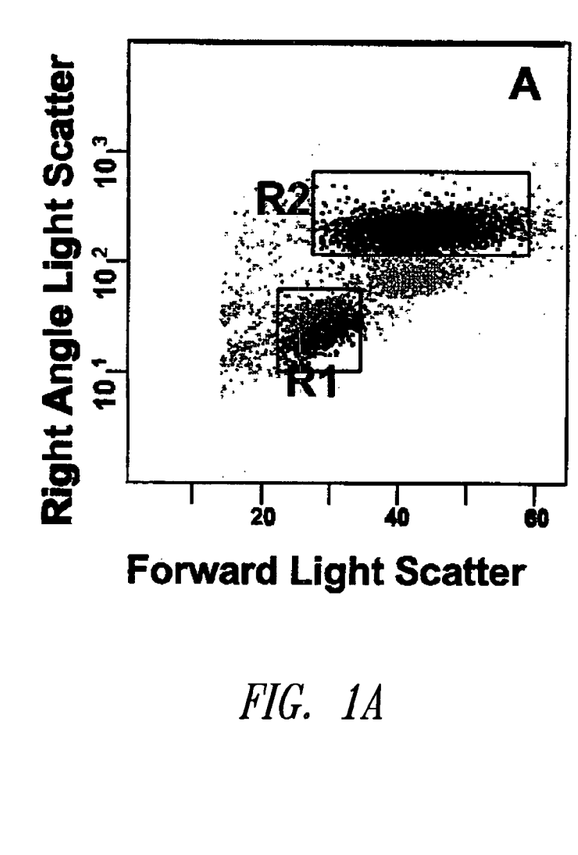
FIG. 1 is a flow cytometric forward and side light scatter plot of unseparated peripheral blood leukocytes.
Figure 1B:
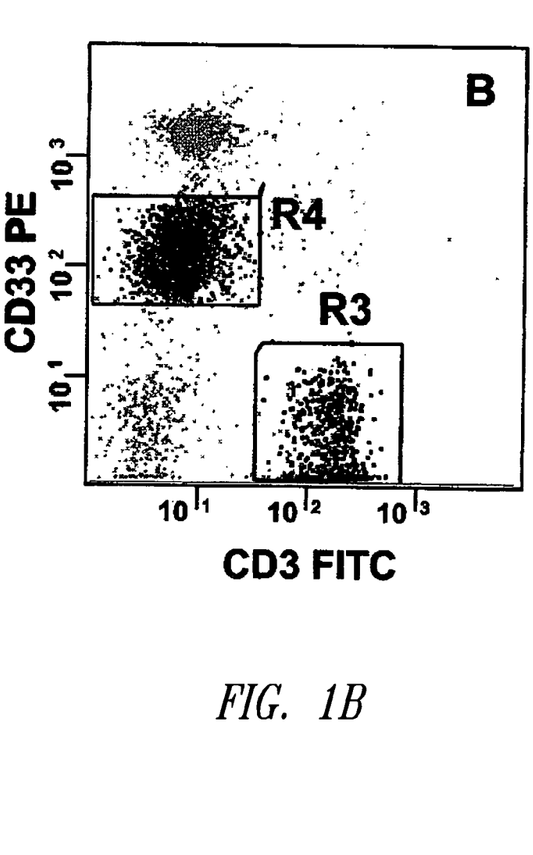

The flow cytometer analyzes the heterogeneous cell population one cell at a time and can classify the cells based on the binding of the immunofluorescent monoclonal antibody and the light scattering properties of each cell (see, for example, Immunol Today. 2000 21(8):383–90). By combining the light scatter properties with the 2 or more colors of immunofluorescent staining, it is possible to unambiguously identify cell populations of interest. For example, using anti-CD3-FITC and anti-CD33-PE antibodies it is possible to unambiguously identify T lymphocytes and granulocytes (neutrophils and eosinophils). This is illustrated in FIG. 1 where peripheral blood leukocytes were stained with anti-CD3-FITC and anti-CD33-PE and analyzed by a flow cytometer (Also see Example 1). In this particular example, lymphoid cells are located in Region R1 based on forward and right angle light scatter. These can be further subdivided based on the expression of CD3 as detected using anti-CD3-FITC which specifically identifies the T lymphoid cells, Region R3. By combining Regions R1 and R3, the T cells within a specimen can be identified, enumerated and sorted. In a similar manner, by combining Regions R2 and R4 the granulocytes (neutrophils and eosinophils) can be specifically identified, enumerated and sorted. These cells are specifically distinguished from B lymphocytes, NK cells, basophils, and monocytes.

As another example, rare cell populations, such as tumor cells or other disease cell types, such as autoimmune cells, cells infected with virus (e.g., HIV), etc. can be detected and isolated using fluorescence activated cell sorting. Rare cell of interest can be detected down to 0.5% or even lower. This technology allows detection of residual disease in a variety of settings, such as in cancer (see, for example, Immunophenotyping, pages 153–160, Eds. C. C. Stewart and J. K. A. Nicholson, 2000 Wiley-Liss, Inc N.Y, N.Y.) and HIV infection.

Using a commercially available fluorescence activated cell sorter, such as the FACSVantage™ (Becton Dickinson, San Jose, Calif.), the EPICS® ALTRA™ (Beckman Coulter, Fullerton, Calif.) or the MoFlo® sorter (DakoCytomation, Inc., Carpinteria, Calif.) cell populations can be sorted into purified fractions. As would be readily recognized by the skilled artisan, a wide variety of cell populations can be-differentiated and sorted using immunofluorescence and flow cytometry.

Solid Supports

As noted above, one technical problem is the difficulty encountered in working with small numbers of purified cells and/or small sample volumes. It is well known in the field that a significant proportion of cells are lost in processing small numbers of cells. It is believed that the cells are lost by adhesion to vessel walls, pipettes or other charged surfaces in which the cells come in contact. Accordingly, the present invention provides methods for collecting sorted populations of cells directly from the cell sorter onto a solid support, for future storage and/or analysis.

Solid supports useful in the context of the present invention generally comprise any material onto which a sample of cells contained in a drop of collection fluid can be absorbed. As such, a support of the present invention is a porous material, generally in the form of a filter membrane as described and defined further herein. Solid supports generally comprise a dry solid matrix comprised of a material with wettability characteristics such that a drop is absorbed in a discrete location on the dry solid matrix. In one embodiment, the discrete location (e.g., the spot) is identifiable, such as by a color indicator (e.g., a pH-type indicator and the like) or a grid marked on the support. "Wettability" refers to the degree to which a solid surface is wetted by a liquid. With respect to water, high-energy surfaces are efficiently wetted and have relatively low contact angles, whereas low-energy surfaces are not wetted and have relatively high contact angles.

In one embodiment of the invention, the solid support is comprised of a porous material or filter media formed either fully or partly from glass, silica or quartz including their fibers or derivatives thereof. Other materials from which the support can be composed also include cellulose-based (nitrocellulose or carboxymethylcellulose papers), hydrophilic polymers including synthetic hydrophilic polymers (e.g. polyester, polyamide, carbohydrate polymers), polytetrafluoroethylene, such as Empore™ (3M, St. Paul, Minn.), fiberglass and porous ceramics.

Solid supports useful in the context of this invention include, but are not limited to, those described in U.S. Pat. Nos. 5,496,562; 5,756,126; 5,807,527; 6,645,717; 6,447,804; 6,627,226; 6,322,983; 6,294,203; and 6,124,012. A suitable solid support of the invention includes two-dimensional flat dry matrices or three-dimensional matrices such as a matrix combined with a binder to form a pellet or tablet. Suitable solid supports are commercially available, through, for example, Whatman (Kent, UK), Fisher Scientific (Hampton, N.H.), Millipore (Billerica, Mass.) and other companies.

The media used for a dry solid matrix of the invention includes any material that does not inhibit the sorption of chemical coating solutions and which does not inhibit the storage and subsequent analysis of nucleic acid-containing material added to it. This includes flat dry matrices or a matrix combined with a binder. In certain embodiments, a dry solid matrix, such as a filter membrane, of the invention is of a porous nature to facilitate immobilization of nucleic acid. In this regard, dry solid matrices useful in the context of this invention enable the specific immobilization of nucleic acid, through an action of cellular lysis. In one embodiment, a dry solid matrix of the invention is such that nucleic acid immobilized to it can remain so in a stable form, not exhibit degradation, shearing, endonuclease digestion, nor UV damage. In certain embodiments, the material, and any chemical solutions sorbed thereto, does not inhibit elution of the nucleic acid-containing material from the dry solid matrix.

As noted above, in certain embodiments, the solid supports of the present invention comprise a dry solid matrix that has been treated with a composition such that cells deposited onto the solid matrix are lysed and the GM from the cells is sorbed, immobilized, and protected from degradation, such as described in U.S. Pat. No. 6,645,717. In this regard, the solid support of the invention includes a composition, such as a lysing agent and/or a genetic material preservative sorbed to a dry solid matrix. As used herein, the term "sorb" means that a composition is absorbed, adsorbed or otherwise incorporated into or onto a solid matrix in such a way as not to be readily removed from the matrix unless subjected to conditions which are intentionally or inadvertently performed to remove the sorbed composition from the solid matrix. In one embodiment, the sorbed composition is not readily removed under normal storage conditions.

The term "chemical coating solution" as used herein means a chemical composition that is able to sorb to the aforementioned dry solid matrices such as filter membranes. The composition of the chemical coating solution, such as a lysing agent and/or a genetic material preservative, is as described and relates to that outlined in U.S. Pat. Nos. 5,756,126, 5,807,527, and 5,496,562.

More specifically, in certain embodiments, the chemical coating solution includes a protein denaturing agent and a free radical trap. The denaturing reagent can be a surfactant that will denature proteins and the majority of any pathogenic organisms in the sample. Anionic detergents, such as sodium dodecyl sulphate (SDS) and sodium lauryl sarcosinate (SLS), are examples of such denaturing reagents. The chemical solution can include a weak base, a chelating agent, and the anionic surfactant or detergent, and optionally uric acid and urate salt as discussed in detail in U.S. Pat. No. 5,807,527. In one embodiment, the weak base can be a Tris, trishydroxymethyl methane, either as a free base or as the carbonate, and the chelating agent can be EDTA, and the anionic detergent can be sodium dodecyl sulfate.

As used herein, a "free radical trap" is a reactant with a free radical and which is sufficiently stable not to generate damaging free radicals itself. Examples of a suitable free radical trap includes: uric acid or a urate salt, mannitol, benzoate (Na, K, Li or tris salt), 1-3 dimethyl uric acid, guanidine, guanine, thymine, adenine, cytosine, in N-acetyl-histidine, histidine, deferoxamine, dimethyl sulfoxide, 5'5' dimethyl pyrroline-N-oxide, thiocyanate salt and thiourea. Illustrative free radical traps include mannitol, thiocyanate salts, uric acid or a urate salt. The longer the period of time for which the GM is to be stored the more likely that a free radical trap may be advantageously included in the composition sorbed to the solid matrix. However, even if the GM is only to be stored for a matter of minutes, a free radical trap may still be incorporated into the composition As used herein, a "weak base" suitable for a composition to be sorbed to a dry solid matrix may be a Lewis base which has a pH of about 6 to 10, and in one embodiment, about pH 8 to 9.5. One function of the weak base may be to act as a buffer to maintain a composition pH of about 6 to 10 or about pH 8.0 to 9.5, for example, pH 8.6. Hence, a weak base suitable for a composition of the invention may, in conjunction with other components of the composition, provide a composition pH of 6 to 10 or about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, tris-hydroxymethyl amino methane (Tris), ethanolamine, triethanolamine and glycine and alkaline salts of organic acids (e.g., trisodium citrate). In one embodiment, the organic weak base is a weak monovalent organic base, for example, Tris. The weak base may be either a free base or a salt, for example, a carbonate salt.

Without being bound by theory, it is believed that the weak base may provide a variety of functions, including protecting the GM from degradation. In addition to providing a buffer system, it is also believed that the weak base can act to ensure proper action of the chelating agent in binding metal ions. In addition, the weak base may also prevent the action of acid nucleases which may not be completely dependent on divalent metal ions for functioning.

The composition sorbed to the dry solid matrix can also include a chelating agent. As used herein, a chelating agent is any compound capable of complexing multivalent ions including Group II and Group III multivalent metal ions and transition metal ions (e.g., Cu, Fe, Zn, Mn, etc). According to the invention, a chelating agent may be a strong chelating agent such as ethylene diamine tetraacetic acid (EDTA). Chelating agents such as a citrate or oxalate are also suitable. The chelating agent may be added to the composition simultaneous with application of a sample of GM to the dry solid medium.

Other coatings having similar function can also be utilized in accordance with the present invention. The term "functionally associated with" means that the coating is disposed, sorbed, or otherwise associated with the support of the present invention such that the support and coating function together to immobilize nucleic acid thereon through an action of cellular lysis of cells presented to the support. That is, the coating can be adsorbed, absorbed, coated over, or otherwise disposed in functional relationship with the media. For example, the support, in the form of a filter membrane, can be disposed in a solution containing the chemical solution. As stated above, in certain embodiments, the support of the present invention is a porous filter media and can be in the form of a flat, dry media. The media can be combined with a binder, examples of binders well-known in the art being polyvinylacrylamide, polyvinylacrylate, polyvinylalcohol, gelatin, for example. In one particular embodiment, the support of the present invention is capable of releasing the GM immobilized thereto by a heat elution. In certain embodiments, such a heat elution is accomplished by the exposure of the support having the GM stored thereon to heated water, the water being nuclease free. Accordingly, in certain embodiments, the dry solid matrix for use in the methods of the invention is such that at any point during a storage regime, it allows for the rapid purification of immobilized nucleic acid. In this regard, the matrix is such that immobilized nucleic acid may be collected in the form of a soluble fraction following a simplified elution process, during which immobilized nucleic acid is released from the dry solid matrix, e.g., filter membrane. The dry solid matrix for use in the invention yields nucleic acid of sufficient quality that it does not impair downstream analyses such as polymerase chain reaction (PCR), ligase chain reaction (LCR), transcription mediated amplification (TMA), reverse transcriptase initiated PCR, DNA or RNA hybridization techniques, sequencing, and the like.

In certain embodiments, the solid supports described herein may include components for subsequent genetic analysis, such as described in U.S. Pat. No. 6,447,804.

To prepare a dry solid matrix of the invention, one or more lysing agents, e.g., compositions as described herein that lyse cells, and/or one or more genetic material preservatives e.g., compositions that protect against degradation of GM, is sorbed to the solid matrix. As used herein, the phrase "protects against degradation of GM" means that a dry solid matrix of the invention maintains the stored GM in a substantially nondegraded form. This provides a sample of GM suitable for many different types of subsequent analytical procedures. Protection against degradation of GM may include protection against substantial damaging of GM due to GM damaging events such as that caused by chemical or biological agents including action of bacteria, free radicals, nucleases, ultraviolet radiation, oxidizing agents, alkylating agents, or acidic agents (e.g., pollutants in the atmosphere).

Collection Onto a Solid Support

The purified cells collected using a flow cytometer as described herein are deposited directly onto a solid support. As noted above, in certain applications, one technical problem is the difficulty encountered in working with small numbers of purified cells and/or small sample volumes. It is well known in the field that a significant proportion of cells are lost in processing small numbers of cells. Accordingly, the present invention provides methods for collecting sorted populations of cells directly from the cell sorter onto a solid support for future storage and/or analysis, thereby virtually eliminating the loss of cells.

A desired number of cells is collected using the parameters of the flow cytometer according to established protocols known to the skilled artisan and as described in the art, for example, in *Current Protocols in Cytometry* (John Wiley & Sons, NY, N.Y., Eds. J. Paul Robinson, et al.). The cells are collected into one or more drops of collection fluid. In one embodiment, single cells are collected in each small drop of collection fluid. As the cells are collected, the drops containing the desired sorted, purified population of cells (fraction) are deposited onto the solid support. In certain embodiments, each fraction of sorted cells containing a distinct population of cells is collected into drops of collection fluid and is deposited onto a separate solid support. In this regard, the solid support may comprise a color indicator wherein, when the drops containing cells of interest are absorbed thereto, the color changes. In this manner, the location of the spot containing the cells and the GM therefrom, is identifiable. In another embodiment, two or more cell fractions, each containing a distinct population of cells, may be deposited onto the same solid support, drops containing a cell or cells from each fraction (i.e., population of sorted cells) being deposited at a distinct, identifiable location on the solid support. In one embodiment, the distinct locations, e.g., spots, are identified through a color indicator incorporated into the solid support or by a grid marked on the solid support using an appropriate marking utensil. Many distinct populations of cells can be sorted, as defined by immunofluorescent markers as described herein. Accordingly, 1, 2, 3, 4, 5, 6, or more distinct populations (fractions) of cells can be sorted and collected as described herein.

The collection drops are generally about $2 \times 10^{-3}$ μl/drop in volume and contain a singe cell. In one embodiment, at least 1, 5, 10, 50, 100, 200, 300, 400, 500, 600, 700, 800, 900, 1,000, 5,000, or 10,000 cell-containing drops are collected at a single location, each location absorbing from about 0.25 μl to about 25 μl, and any volume there between, of collection fluid containing cells. In certain embodiments, the drops may contain more than one cell.

In one embodiment, the solid support for collecting cells is placed on a manifold specifically designed to fit into a flow cytometer of choice, such as the FACSVantage™ SE (Becton Dickinson, San Jose, Calif.). One such manifold is shown in FIG. 4. In this regard, a manifold can be used in conjunction with the solid supports described herein, such as Indicating FTA Micro Cards (Whatman BioScience, Kent, UK) for acquiring cell populations and GM therefrom for future storage and/or analysis.

Once deposited on the solid support, the spot is allowed to dry at room temperature.

Subsequent Analysis of Genetic Material Stored on the Dry Solid Matrix

Generally, the genetic material sorbed to the solid support as described herein can be analyzed using any of a variety of molecular biological techniques known in the art. Examples of subsequent analysis which may be performed on samples of GM stored on the dry solid medium include, but are not limited to, polymerase chain reaction (PCR), ligase chain reaction (LCR), reverse transcriptase initiated PCR (RT-PCR), DNA or RNA hybridization techniques including restriction fragment length polymorphism (RFLP) and other techniques using genetic probes such as fluorescence in situ hybridization (FISH), DNA analysis by variable number of tandem repeats (VNTR) or short tandem repeats (STR), or other genotype analysis, CpG methylation analysis (see for example, Cottrell, et al., *Nucleic Acids Research*, 2004, Vol. 32, No. 1 e10), genomic sequencing, enzymatic assays, affinity labeling, methods of detection using labels or antibodies and other similar methods.

The genetic material can be analyzed using any desired technique as described further herein, directly on the solid support or the genetic material may be eluted into aqueous solution prior to analysis, depending on the particular solid support used for collection.

Generally, once the samples collected onto the solid support are dry, a sample disc can be taken from the desired spot using a coring device. Generally, a disc from about 1.0 mm to about 2.0 mm is sufficient. As noted above, analysis may be carried out directly on the solid support, or the genetic material may be eluted using techniques known in the art, or as described in U.S. Pat. No. 6,645,717.

In certain embodiments, the disc containing genetic material is first washed with a series of purification reagents known in the art, such as described in Example 1. For example, to each tube containing a single 1 mm disc punch, 200 µl of FTA Purification Reagent (Fitzco, Inc, Spring Park, Minn.) is added. (Per 500 ml: 0.29 g NaCl; 5 ml 1 M Tris pH 7.5; 1 ml 0.5 M EDTA; 2.5 ml TRITON-X-100 (t-Dc-tylphenoxypolyethoxyethanol), a non-ionic surfactant.) Following incubation for several minutes at room temperature, the FTA purification Reagent is aspirated from the tube and the process is repeated one to two more times, as needed. Two hundred µl of TE (10 mM Tris-HCl, 1 mM EDTA, pH 8.0) buffer is then added to each tube. The tubes are incubated for about five minutes at room temperature and the TE buffer is then fully aspirated from both tubes, leaving the now washed 1 mm disc at the bottom of each tube. If analysis is carried out directly on the solid support, the disc is dried and subsequent analysis is carried out directly. Otherwise, nuclease free water can be applied to the tube and the tube incubated at 95° C., or at a temperature sufficient for efficient elution of the bound genetic material, for about 10 minutes. Following heat incubations the nuclease free water, now containing the eluted genetic material, is aspirated from each tube and retained. PCR or other molecular genetic analysis can then be carried out as desired following any of a variety of parameters known to the skilled artisan.

These techniques for analyzing genetic material are well known in the art and are described for example, in *Current Protocols in Molecular Biology* (John Wiley & Sons, NY, N.Y.), or Innis, Ed., *PCR Protocols*, Academic Press (1990).

As would be recognized by the skilled artisan, the above methods can be used in a number of settings, including but not limited to diagnostics and disease and treatment monitoring.

From the foregoing it will be appreciated that, although specific embodiments of the invention have been described herein for purposes of illustration, various modifications may be made without deviating from the spirit and scope of the invention. The following Examples are offered by way of illustration and not by way of limitation. Accordingly, the invention is not limited except as by the appended claims.

EXAMPLES

Example 1

Cell Sorting and Genotype Analysis of T Lymphocytes and Granulocytes

This example describes the genotype analysis of T lymphocytes and granulocytes purified using a flow cytometer and collected directly onto a solid support.

Blood was collected from a patient who had undergone a hematopoietic stem cell transplant. Mature erythrocytes were lysed using buffered $NH_4Cl$. The remaining leukocytes were washed and then incubated with monoclonal antibodies anti CD3-conjugated to fluorescein isothiocyanate (anti-CD3-FITC) and anti CD33-conjugated to phycoerythrin (anti-CD33-PE). After about 20 minutes of incubation in the dark the leukocytes were washed with buffered saline and resuspended in buffered saline containing protein (e.g., fetal calf serum) for introduction into the flow cytometer.

The flow cytometer instrument settings used were made by an experienced instrument handler to adjust appropriately for compensation and detector voltages. As would be recognized by the skilled artisan, the use of different detection antibodies with different fluorescent tags requires unique adjustment to any particular instrument to give optimal signal separation (voltage) with minimal "bleeding-over" into other channels (e.g., compensation). A skilled flow operator, well-versed in using compensation controls, isotype controls, and with a general understanding of cell biology should be able to reproduce any of the data presented below.

Further it should be noted that various settings, particularly voltage settings, may vary, depending upon the efficiency of the instrument laser. For example, older lasers may require more voltage to generate a signal comparable to a newer laser. However, the data obtained, whether with more or less voltage, should reflect similar patterns in biology.

Using accepted flow cytometric parameters (such as described in *Current Protocols in Cytometry*, John Wiley & Sons, NY, N.Y., Eds. J. Paul Robinson, et al.), it was possible to unambiguously identify T lymphocytes and granulocytes (neutrophils and eosinophils) (see FIG. 1 and FIG. 2). In FIG. 1, peripheral blood leukocytes were stained with anti-CD3-FITC and anti-CD33-PE and analyzed as described above. Lymphoid cells are located in Region R1 based on forward and right angle light scatter. These can be further subdivided based on the expression of CD3 as detected by anti-CD3-FITC which specifically identifies the T lymphoid cells, Region R3. By combining Regions R1 and R3, the T cells within a specimen were identified, enumerated and sorted. In a similar manner, by combining Regions R2 and R4 the granulocytes (neutrophils and eosinophils) were specifically identified, enumerated and sorted. These cells are specifically distinguished from B lymphocytes, NK cells, basophils, and monocytes.

Figure 2A:
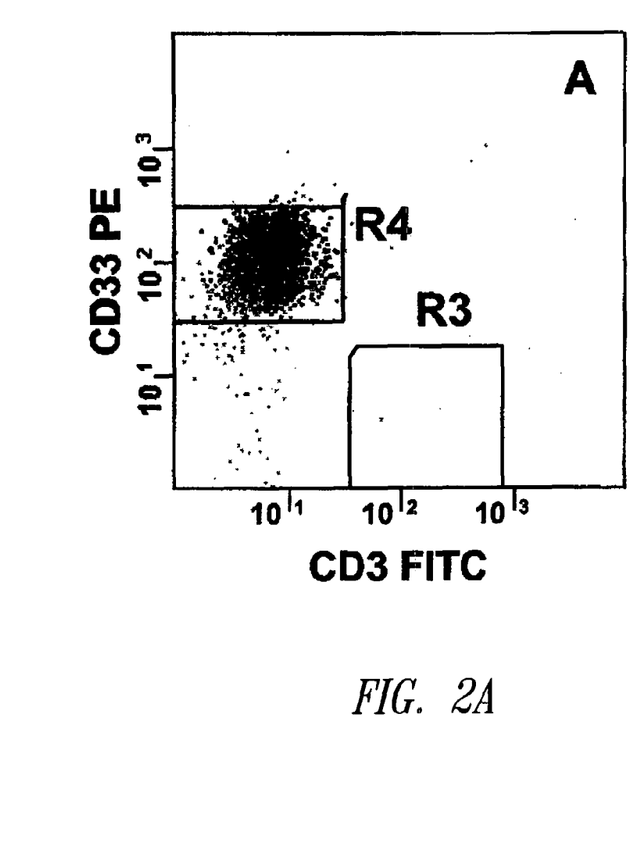
FIG. 2 is a flow cytometric CD3-FITC/CD33-PE-plot showing purified granulocytes (A) and T cells (B).
Figure 2B:
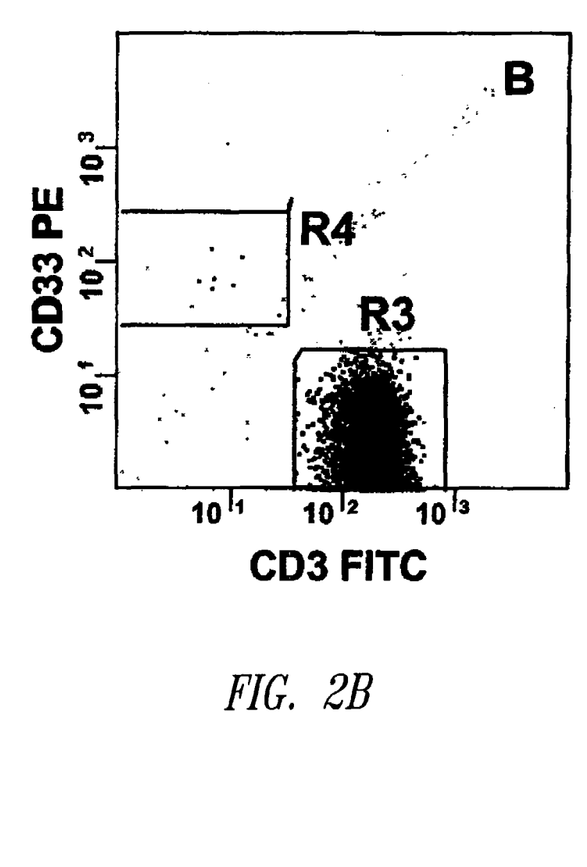

Using a fluorescence activated cell sorter, such as the FACS Vantage (Becton Dickinson, San Jose Calif.) these two populations were sorted into purified fractions. Upon reanalysis of these purified fractions it was shown that >98% purity is generally obtained for each fraction (FIG. 2). Thus, these two cell lineages were separated to >98% purity with a single 2 color reagent combination.

Figure 3A:
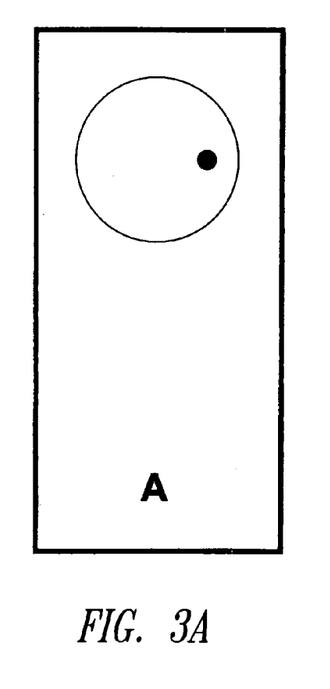
FIG. 3 is a diagram showing the position of purified granulocytes (A) and T lymphocytes (B) on FTA filter paper after cell sorting.
Figure 3B:
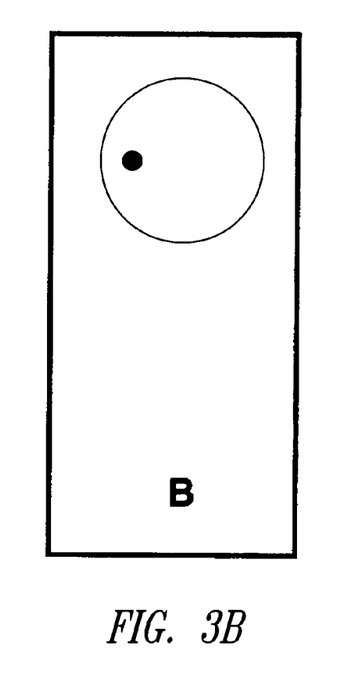
Figure 4A:
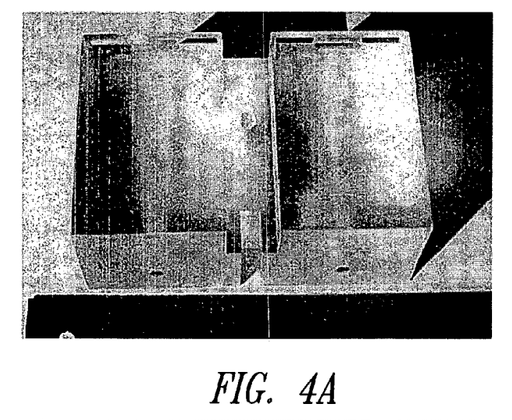
FIGS. 4A–4D show photographs of a manifold built specifically for use on Becton Dickinson Vantage™ SE used to collect sorted cells onto Indicating FTA® Micro Card from Whatman BioScience (Kent, UK) for acquiring, holding, and/or transporting sorted cells for future analysis and archive.
Figure 4B:
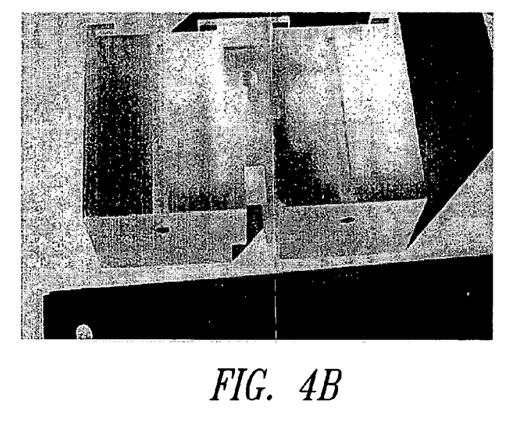
Figure 4C:
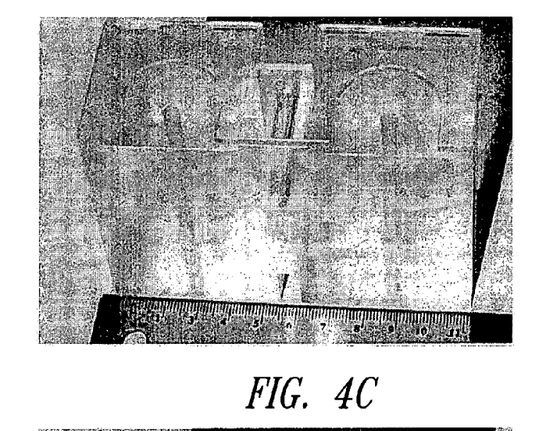
Figure 4D:
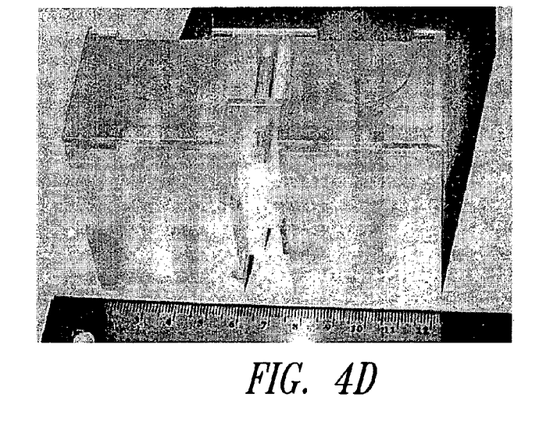

The two cell populations were then sorted (1,000 cells/2 µl) and were each deposited on a separate FTA® Card (Whatman, Kent, UK). As shown in the diagram of FIG. 3, the purified granulocytes were deposited on the right side of one FTA® Card while the T lymphocytes were deposited on the left side of another FTA® Card. Thus, the position of the spot on the card was an additional identification marker as to the origin of the cells.

The spots were allowed to dry at room temperature and a punched disc was taken from each spot using a coring device. The card containing the remainder of the spot was archived for later use. The genetic material on the punched disc was then prepared for analysis according to the manufacturer's recommendations as follows. Each disc was placed in a PCR amplification tube with 200 µl of FTA Purification Reagent (Whatman) for 5 minutes. The FTA Purification Reagent was then removed with a pipette, and the above step was repeated 2 more times for a total of 3 washes. Next, 200 µl of TE Buffer was added to the tube and incubated for 5 minutes at room temperature. The TE was removed and the wash repeated once more. The disc was then dried at room temperature. The disc may also be dried using mild heat (e.g., 56° C.).

The DNA was then used for genetic analysis using molecular biological techniques.

By combining these techniques of identification of specific cell populations by flow cytometry and specimen preservation on specialized paper, it was possible to sort purified fractions of T lymphocytes and granulocytes directly onto the filter paper. This eliminated the need for manipulation of the often very small numbers of cells and allowed for long term preservation of the specimen. Routinely, only 2,000 cells need to be sorted directly onto the filter paper. This number compares to the 15,000–20,000 cells needed to be sorted into tubes for a similar analysis. In additional experiments, as few as 200 cells were successfully analyzed as described above. Further, all isolated cells may not be needed for molecular analysis so the remainder can be easily and safely archived for additional analysis at a later time.

In a clinical setting standardization of techniques is highly desirable. With this technique, a specimen can be stained with anti-CD3-FITC and anti-CD33-PE in the same tube. Therefore the two fractions come from a single processing. Standardization of the direction of sorting and collection from the sorter (e.g., left or right) and sample position on the collection filter (FIG. 3) further improves sample collection procedures.

Example 2

Cell Sorting Mixed Chimerism Validation Analysis

This example describes a mixed chimerism study carried out to validate cell sorting of mixed chimeric cell populations onto FTA cards. The results showed that sorting T cells and granulocytes followed by genetic analysis is accurate down to as low as 200 total sorted cells.

Unrelated male and female blood was mixed to simulate different levels of chimerism. Different percentages of male and female cells were mixed ranging from 0% male/100% female to 100% male/0% female. Each fraction mixture was then analyzed by first sorting CD3+ T cells and CD33+ granulocytes onto FTA cards essentially as described in Example 1 and then analyzing the sorted cells using short tandem repeats (STR; Promega, Madison, Wis.) DNA analysis. Since the STR analysis detected multiple differences, including male/female, the averages of all the differences were used to determine the mixture proportions. The results showed a very tight relationship between the expected and assayed proportions of the two individuals in the mixed cell populations, further confirming the validity of the assay.

In a related experiment, two unrelated peripheral blood specimens were mixed. CD3+ T cells and CD33+ granulocytes were then sorted onto FTA cards essentially as described in Example 1. In this experiment, different total numbers of cells were sorted. STR analysis of the sorted cells (averaging multiple markers) showed that the proportion of each individual detected is not affected by cell number from 2000 cells even down to 200 total sorted cells. The determined and expected results were the same over this range of cells for T lymphocytes and for granulocytes. This demonstrates that sorting as few as 200 cells is still effective for accurate genetic analysis.

What is claimed is:

1. A method for collecting purified cells and genetic material therefrom for genetic analysis, comprising:

sorting a population of cells using a flow cytometer and collecting a purified cell in a drop of collection fluid;

depositing the drop of collection fluid onto a solid support at a discrete location, the solid support comprising a cell lysing agent and a genetic material preservative;

wherein the purified cell within the drop of collection fluid is absorbed by the solid support and lysed by the lysing agent to yield genetic material;

and wherein the genetic material is sorbed by the solid support and protected from degradation by the genetic material preservative;

thereby collecting purified cells and genetic material therefrom for genetic analysis.

2. The method according to claim 1 wherein the solid support is comprised of a cellulose-based substance.

3. The method according to claim 2 wherein the substance is selected from the group consisting of cellulose, nitrocellulose and carboxymethylcellulose.

4. The method according to claim 1 wherein the solid support is comprised of hydrophilic polymers.

5. The method of claim 4 wherein the hydrophilic polymers are selected from the group consisting of polyester, polyamide, and carbohydrate polymers.

6. The method of claim 1 wherein the solid support is comprised of a substance selected from the group consisting of glass, silica and quartz fibers.

7. The method of claim 1 wherein the discrete location is identifiable by a color indicator.

8. The method of claim 1 wherein two or more drops of collection fluid are deposited onto the same solid support.

9. The method of claim 8 wherein the two or more drops of collection fluid are deposited at the same discrete location.

10. The method of claim 1 wherein at least a first and a second population of cells are sorted and wherein a drop of collection fluid containing a cell from the first population and a drop of collection fluid containing a cell from the second population are deposited each onto a separate solid support.

11. The method of claim 10 wherein the drop of collection fluid containing a cell from the first population and the drop of collection fluid containing a cell from the second population are deposited each at a distinct location onto the same solid support.

12. The method of claim 1 further comprising releasing the genetic material sorbed onto the solid support by heat elution.

13. The method of claim 1 further comprising analyzing the genetic material using a polymerase chain reaction.

14. The method of claim 1 further comprising analyzing the genetic material using short tandem repeats.

15. The method of claim 1 wherein the population of cells comprises leukocytes.

16. The method of claim 15 wherein the leukocytes are incubated with a dye-conjugated monoclonal antibody that is specific for a marker selected from the group consisting of CD3, CD33, CD34, CD8, CD4, CD56, CD19, CD14, CD15, CD16, CD13, CD38, CD45, CD20, CD5, CD2 and CD10.

17. The method of claim 15 wherein the leukocytes are incubated with a dye-conjugated monoclonal antibody that is specific for CD3 and a dye-conjugated monoclonal antibody that is specific for CD33 prior to sorting.

18. The method of claim 17 wherein the leukocytes are incubated with the dye-conjugated monoclonal antibody that is specific for CD3 and the dye-conjugated monoclonal antibody that is specific for CD33 in the same tube.

* * * * *